US006936635B1

(12) United States Patent
Da Silva

(10) Patent No.: US 6,936,635 B1
(45) Date of Patent: Aug. 30, 2005

(54) COMPOSITION FOR THE TREATMENT OF RESPIRATORY DISORDERS AND A METHOD FOR ITS USE

(76) Inventor: Benedito Da Silva, Rua Joaquim Murtinho, 62, Apt. 201, Santo Antonio, CEP-30350-050, Belo Horizonte (BR)

( * ) Notice: Subject to any disclaimer, the term of this patent is extended or adjusted under 35 U.S.C. 154(b) by 0 days.

(21) Appl. No.: 09/868,793

(22) PCT Filed: Dec. 17, 1999

(86) PCT No.: PCT/BR99/00107

§ 371 (c)(1),
(2), (4) Date: Oct. 1, 2001

(87) PCT Pub. No.: WO00/37069

PCT Pub. Date: Jun. 29, 2000

(30) Foreign Application Priority Data

Dec. 21, 1998 (BR) ................................. 9805767

(51) Int. Cl.$^7$ ............................................. A61K 31/19

(52) U.S. Cl. ..................................................... 514/557

(58) Field of Search ....................................... 514/557

(56) References Cited

FOREIGN PATENT DOCUMENTS

| DE | 2721014 A | * | 11/1978 |
| JP | 63170323 A | * | 7/1988 |
| JP | 6-211649 | | 8/1994 |

OTHER PUBLICATIONS

Remington's Pharmaceutical Scineces, 15$^{th}$ edition, 1975, p. 1443.*
Minna Kaila et al., "Enchancement of the Circulating Antibody Secreting Cell Response in Human Diarrhea by a Human Lactobacillus Strain" Pediatric Research (1992) vol. 32, No. 2 pp. 141-144.
L. Saucier, et al., "Effect of Feeding Lactic Acid Bacteria and Fermented Milk on Specific and Nonspecific Immune Responses of Mice Infected with *Klebsiella pneumoniae* AD-1" Journal of Food Protection. vol. 55, Aug. 1992, pp. 595-600.
Gabriela Perdigon, et al., "Effect of Yogurt Feeding on the Small and Large Intestine Associated Lymphoid Cells in Mice" Journal of Dairy Research (1994), pp. 553-562.

Maria E. Nader De Macias, et al., "Inhibition of *Shigella sonnei* by *Lactobacillus casei* and *Lact. acidophilus*" Journal of Applied Bacteriology (1992) pp. 407-411.
Erika Isolauri, et al., "*Lactobacillus casei* Strain GG Reverses Increased Intestinal Permeability Induced by Cow Milk in Suckling Rats" Gastroenterology (1993) vol. 105, No. 6, pp. 1643-1650.
Ikuo Kato, et al., "Effects of Oral Administration of *Lactobacillus casei* on Antitumor Responses Induced by Tumor Resection in Mice" Pergamon Press Ltd., Internal Journal of Immunopharacology (1993), pp. 29-36.
Gabriela Perdigon, et al., "Effect of Viable *Lactobacillus casei* Feeding on the Immunity of the Mucosae and Intestinal Microflora in Mal-nourished Mice" Milchwissenschaft 50 5 (1995), pp. 251-256.
Blanca Solis Pereyra, et al., "Induction of Human Cytokines by Bacteria Used in Dairy Foods" Nutrition Research, vol. 13, pp. 1127-1140 (1993).
E.J. Schiffrin et al., "Immunomodulation of Human Blood Cells Following the Ingestion of Lactic Acid Bacteria" Journal of Dairy Science vol. 78, No .3 (1995), pp. 491-497.
C. De Simone, et al., "Effect of *Bifidobacterium bifidum* and *Lactobacillus acidophilus* on Gut Mucosa and Peripheral Blood B Lymphocytes" Immunopharmacology and Immunotoxicology, (1992) vol. 14, pp. 331-340.
Haruki Kitazawa, et al., "Expression of mRNA Encoding IFNA in Macrophages Stimulated with *Lactobacillus gasseri*" FEMS Microbiology Letters, (1994) vol. 120, pp. 315-322.
Erika Isolauri, et al., "Improved Immunogenicity of Oral D X RRV Reassortant Rotavirus Vaccine by *Lactobacillus casei* GG " (1995) Vaccine, vol. 13, pp. 310-312.
Myrvik QN (1993); Immunology and Nutrition, Modern Nutrition in Health and Disease, ed. ME Shils, JA Olson, M Shike. London: Lea & Febiger, pp. 623-662.
JP 63170323 A (Abstract Only).

* cited by examiner

Primary Examiner—Rebecca Cook
(74) Attorney, Agent, or Firm—Cantor Colburn LLP

(57) ABSTRACT

The present invention relates to a composition comprising alpha-hydroxy propionic acid linked to any pharmaceutically acceptable vehicle, such as pure serum, 1,2,3-propanetriol, 1,2-propanediol resp. a mixture thereof or optionally a pharmaceutically acceptable catalyzer. Alpha-hydroxypropionic acid is used in medicine in many dilutions for the treatment of sinusitis and other upper respiratory diseases. The present invention is characterized by a formulation adapted to nasal delivery for the treatment of upper respiratory disorders.

13 Claims, No Drawings

COMPOSITION FOR THE TREATMENT OF RESPIRATORY DISORDERS AND A METHOD FOR ITS USE

This is a 371 of PCT/BR99/00107 filed Dec. 17, 1995.

TECHNICAL FIELD

The present invention relates to a composition for the treatment of sinusitis and rhinitis and other respiratory disorders. The composition comprises alpha-hydroxypropionic (or 2-hydroxyl-propionic), popularly known as Lactic Acid, linked to an appropriate vehicle so that it may be used via the nasal airways.

BACKGROUND OF THE INVENTION

Presently, there is no efficient medication for sinusitis and rhinitis treatment. Rather, treatment for these disorders lies primarily in the use of antibiotics. Aside from being economically costly, current antibiotic treatment poses a substantial risk to the public health as overuse results in antibiotic resistance. Antibiotic treatment also has limited applicability in the treatment of respiratory disorders, such as sinusitis. As known, sinusitis is an inflammation of the layer of the tissue that internally covers the cheekbones through little holes (sinuses) that communicate with the nasal cavity directly linked to the external environment. For a biologically active substance to carry out its duty, it is desirable to be positioned at the action location. The active principles are taken into the body through medicines. Therefore it is desirable for them to be released in the location where the infectious agents are. In fact, the antibiotic is a medicine for internal use and that is why it is not efficient in the sinusitis treatment, taking into consideration that its release does not occur at the infection spot. Rather, antibiotic treatment typically begins once the patient suffering from the respiratory disorder is in acute crisis. During the crisis stage, germs located in external areas of the organism or in close contact with the external environment, i.e., in the nasal cavity or in the sinuses of the cheekbones, are not reached. Accordingly, the use of antibiotics is inefficient in the treatment of respiratory disorders such as sinusitis and rhinitis.

SUMMARY OF THE INVENTION

The present composition aims at solving the above problems, being especially produced for application through the nasal airways. The composition comprises an alpha-hydroxypropionic acid or an acceptable pharmaceutical dilution thereof, linked to an appropriate vehicle applied through the nasal cavities of patients in need thereof.

DETAILED DESCRIPTION OF THE INVENTION

The composition of the present disclosure comprises an active compound including alpha-hydroxypropionic acid, a pharmaceutical salt of alpha-hydroxypropionic acid, or a pharmaceutical catalyzer of alpha-hydroxypropionic acid, wherein the active compound maybe linked to an appropriate vehicle for application through the nasal cavities of a patient in need thereof. The vehicle may be a serum or any other pharmaceutical capable of carrying the active compound through the nasal cavities, A preferred vehicle comprises 1,2,3-propanotriol (glycerin), 1,2-propanodiol, and mixtures of at least one of the foregoing. Acceptable dilutions of the active compound in the vehicle are 0.2 ml to 4 ml active compound for each 100 ml of the vehicle (0.2 to 4 vol % of active compound based on the volume of the vehicle), or even 0.2 mL to 1 mL of the active compound for each 100 mL of the vehicle (0.2 to 1.0 vol % of active compound based on the volume of the vehicle). Additionally, where the vehicle is 1,2-propanodiol, a particularly preferred dilution of the active compound in the vehicle is 0.2 ml to 10.0 ml of the active compound for each 10 ml of the vehicle.

The suggested dosage is in an amount that will result in desired effects obtained during the application of the composition. The composition may be taken by drops, spray, microfine powder, or as a pharmaceutical salt via the nasal airways. As the application of the composition occurs at the nostrils, such a compound will work directly on the germs located in the nasal cavities and cheeks. The composition may be used to treat upper respiratory disorders such as sinusitis.

The first application effect of the composition in the nasal cavities and cheekbones is dehydration of the germs that can be found there through its bactericide and bacteriostatic properties. After that, the hydrating and moistening effects of the composition cause the increase in the nasal mucosa elasticity and its clearance. The action motion of the alpha-hydroxypropionic acid keeps a more homogeneous cornea layer, decreasing the superficial cellular cohesion. The alpha-hydroxypropionic acid promotes a subtle exfoliation, leaving the nasal mucosa smoother and more homogeneous. Therefore, the composition may be used effectively as a nasal releaser.

The composition effects media changes in the areas to which it is exposed. That is, the composition modifies the medium pH, facilitating growth of *Lactobacyllus acidophyllus* and *Bifidobacteria* bacteria. Growth of *Bifidobacteria* has beneficial effects upon the host organism. For example, *Bifidobacteria* are known for displaying inhibiting effects, both in vitro and in vivo, upon many other pathogenic germs, such as *Candida albicans, Shighellas, Clostridium, Bacillus cereus, Staphylococcus aureus,* and *Campylobacter jejuni.* Thus, the compositions comprising alpha-hydroxypropionic acid are suitable for the treatment of sinusitis caused by bacterial and fungal organisms, i.e. germs.

It is known that *Bifidobacteria* in the large intestine synthesize beneficial vitamins that are absorbed by the organism. *Bifidobacteria* are known for producing thiamine, riboflavine and vitamins B6 and K. It's still proved that the *Bifidobacteria* are able to synthesize complex B vitamins. It is believed that the *Bifidobacteria*, by competition, also remove from the large intestines putrefying bacteria which are responsible for the release of free radicals. Free radicals, which are absorbed by the host organism, tend to create harm to the host, such as early aging.

Similarly to the gastrointestinal tract, the respiratory system is open to the external environment in order to facilitate the host organism's breathing. In the cheekbones, the present medication changes the medium pH, promoting mucosa hydration which will speed up *Bifidobacteria* growth. The *Bifidobacteria*, by competition, leaves out the pathogenic bacteria, found there, which are responsible for infection of the cheekbones.

One of the *Bifidobacteria* effects as an effective pathogenic germ inhibitor is associated with the production of lactates and acetates in small portions in the mechanism of reaction in the chemical products resultant from the carbohydrates catabolism. Those elements and the pH inhibit the pathogenic bacteria growth. Utilization of the composition is considered by the otorhinolaryngologist clinics as a salutary alternative to rhinitis and sinusitis treatment. Carriers of such diseases feel considerable relief from the very first time they take the composition as disclosed herein. Additionally, the composition has shown advantages upon any other medicine, for it isn't reabsorbed for being a product of cellular rejects.

What is claimed is:

1. A method of treating sinusitis and rhinitis in a human or an animal in need thereof, the method comprising:
   administering to a nasal passageway of the human or the animal a composition comprising alpha-hydroxypropionic acid and a pharmaceutically acceptable vehicle, wherein the alpha-hydroxypropionic acid is in a concentration of 0.2–4 vol. % based on the volume of the acceptable pharmaceutical vehicle; and
   wherein the sinusitis and rhinitis are caused by a bacterial organism or a fungal organism.

2. The method as claimed in claim 1, wherein the pharmaceutically acceptable vehicle comprises 1,2,3-propanotriol, 1,2-propanodiol, serum, or a mixture consisting of at least two of the foregoing.

3. The method as claimed in claim 1, wherein the composition is used as to exfoliate the mucosa of the nasal passages.

4. The method as claimed in claim 2, wherein the pharmaceutically acceptable vehicle is 1, 2,3-propanotriol.

5. The method as claimed in claim 2, wherein the pharmaceutically acceptable vehicle is serum.

6. The method as claimed in claim 2, wherein the pharmaceutically acceptable vehicle is 1,2-propanodiol.

7. The method as claimed in claim 1, wherein the composition is placed into a pharmaceutically acceptable form consisting of drops, a spray, and a fine powder.

8. The method of claim 6, wherein the composition has a ratio of the alpha-hydroxypropionic acid to the 1,2-propanodiol of 1:1 to 1:5.

9. A method of treating an upper respiratory disorder selected from sinusitis and rhinitis in a human or an animal in need thereof, the method comprising:
   administering to a nasal passageway of the human or the animal a composition comprising:
   alpha-hydroxypropionic acid; and
   a pharmaceutically acceptable vehicle comprising 1,2,3-propanotriol, 1,2-propanodiol, serum, or a mixture of at least two of the foregoing vehicles;
   wherein the alpha-hydroxypropionic acid is in a concentration of 0.2–4 vol. % based on the volume of the acceptable pharmaceutical vehicle; and
   wherein the sinusitis and rhinitis are caused by a bacterial organism or a fungal organism.

10. The method of claim 9, wherein the upper respiratory disorder is sinusitis.

11. A method of treating an upper respiratory disorder selected from sinusitis and rhinitis caused by bacteria in a human or an animal in need thereof the method comprising:
   administering to a nasal passageway of the human or the animal a composition comprising alpha-hydroxypropionic acid and a pharmaceutically acceptable vehicle, wherein the alpha-hydroxypropionic acid is in a concentration of 0.2–4 vol. % based on the volume of the acceptable pharmaceutical vehicle.

12. The method of claim 11, wherein the pharmaceutically acceptable vehicle comprises 1,2,3-propanotriol, 1,2-propanodiol, serum, or a mixture of at least two of the foregoing vehicles.

13. The method of claim 11, wherein the upper respiratory disorder is sinusitis.

\* \* \* \* \*